(12) United States Patent
Arida et al.

(10) Patent No.: US 10,295,497 B2
(45) Date of Patent: May 21, 2019

(54) ORGANIC MEMBRANE BASED SCREEN PRINTED MICROCHIP FOR POTENTIOMETRIC DETERMINATION OF LEAD

(71) Applicant: King Abdulaziz City for Science and Technology, Riyadh (SA)

(72) Inventors: Hassan Abdou Arida, Taif (SA); Mohammad Ateeq AlDosari, Riyadh (SA)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 249 days.

(21) Appl. No.: 15/195,142

(22) Filed: Jun. 28, 2016

(65) Prior Publication Data

US 2017/0370873 A1    Dec. 28, 2017

(51) Int. Cl.
*G01N 27/333* (2006.01)
*G01N 33/20* (2019.01)
*G01N 33/18* (2006.01)
*G01N 27/403* (2006.01)
*G01N 27/416* (2006.01)

(52) U.S. Cl.
CPC ..... *G01N 27/3335* (2013.01); *G01N 27/4035* (2013.01); *G01N 27/4163* (2013.01); *G01N 33/1813* (2013.01); *G01N 33/20* (2013.01)

(58) Field of Classification Search
CPC ............. G01N 27/335; G01N 27/4035; G01N 27/4163; G01N 33/1813; G01N 33/20
See application file for complete search history.

(56) References Cited

U.S. PATENT DOCUMENTS

2012/0270756 A1* 10/2012 Collier ............... C12Q 1/00
506/32
2014/0322518 A1* 10/2014 Addleman ........... C09D 183/04
428/304.4

OTHER PUBLICATIONS

H. A. Arida, A Novel Solid-State Copper (II) Thin-Film Micro-Sensor Based on Organic Membrane and Titanium Dioxide Nano-Composites, Int. J. Electrochem. Sci., vol. 9, pp. 426-434 (2014) (Year: 2014).*

(Continued)

*Primary Examiner* — Maris R Kessel
(74) *Attorney, Agent, or Firm* — Geeta Kadambi; Riddhi IP LLC (57) ABSTRACT

A disposable screen-printed microchip based on an organic membrane sensitive layer is presented. The microchip is highly responsive for the determination of Lead(II). The microchip is composed of a composite sensitive material which comprises carbon nano-tubes "CNTs" and titanium (IV) oxide nano-particles embedded in a PVC membrane which was deposited on the surface of a plastic screen printed micro-electrode using a new methodology. The prepared disposable microchip provides a linear response for $Pb^{2+}$ ions covering the concentration range of $1\times10^{-6}$ to $1\times10^{-1}$ mole $L^{-1}$ with high sensitivity (49 mV), a long life span (>4 months) and short response time (10 s). The merits offered by the micro-sensor or microchip include small size, simple fabrication, mass production, integration feasibility and cost effectiveness and automation.

4 Claims, 6 Drawing Sheets

(56) References Cited

OTHER PUBLICATIONS

H. A. Arida, Development of a long-term stable organic membrane-based thin-film microsensor using new-type substrate surface treatment, Talanta, vol. 71, pp. 1856-1860 (2007) (Year: 2007).*
Hampshire College, Lab Safety Manual: Laboratory Use/Procedures and Policies, Sep. 2014 (Year: 2014).*

* cited by examiner

ORGANIC MEMBRANE BASED SCREEN PRINTED MICROCHIP FOR POTENTIOMETRIC DETERMINATION OF LEAD

FIELD OF THE INVENTION

The subject matter disclosed in this application relates generally to the field of potentiometric sensors and electrochemical sensors for the analysis of lead(II).

BACKGROUND OF THE INVENTION

Potentiometric and electrochemical sensor devices have received great attention in the last few years. In the recent past there has been widespread focus on miniaturization and patterning of these sensor devices from bulk to microchips scale.

One of the goals of a manufacturer of electrochemical sensors is to produce sensors that are sufficiently cheap and can be deployed as unit-use devices, thus eliminating or simplifying the analyzer's often very complex fluidics required for the washing and calibrating of multiple-use sensors. To achieve this goal, manufacturers have investigated planar technologies for low cost sensor manufacture. Such planar technologies also purport to provide appropriate control of the materials of construction and manufacturing processes to achieve device-to-device reproducibility in high volume production. Sensors made by planar technology include both thick-film and thin-film micro-fabrication technologies. Thick film processed devices comprise electrodes made by thick film fabrication processes such as plating, screen-printing and dispensing among others. Micro-fabrication technology has proven to have superior dimensional control and has been used to make devices for unit-use applications. Micro-fabrication technology employs wafer-level processes and these devices contain electrodes made by thin-film micro-fabrication processes on various substrates.

Micro-fabrication methodologies of the miniaturized microchips are mainly based on the deposition of a sensitive membrane layer on a micro-sized substrate. In this context, screen-printing is a well-known technique in the micro-fabrication method for realizing micro-sensor assemblies on various substrates (i.e., plastic, ceramics, paper, glass, etc.) [1-3]. Solid-state square planar electrodes particularly screen printed microchips are substrates widely used in the fabrication of chemical sensors responsive for biological species, drugs, toxic elements or heavy metals. These devices with plastic substrates are coated with layers of electro-conductive and insulating inks at a controlled thickness. The screen-printed technology is a modern technology having superior features namely, simple, fast, integration and automation feasibility and can be used in vivo applications. The advantages provided by the screen-printed electrodes are short response times, accuracy, robust, inexpensive, use of small amounts of reagents, miniaturization, large-scale production, small size, disposability, low output impedance and low cost by mass production. Regardless of which of the above variants of planar technology is being used, planar devices of the prior art have been complex to manufacture and are therefore still relatively expensive. In addition in spite of the mentioned advantages of the screen-printed based micro-sensors, such technology is rather rarely applied for the fabrication of potentiometric devices.

In order to improve the selectivity of the potentiometric sensors and ion selective electrodes, significant research effort has been focused on the development and modification of these sensors with nano-particle based sensitive layers [4-11]. Such materials have unique properties and improve the potentiometric response of the electrodes due to the high surface to volume ratio, which is a characteristic feature of such materials [5,6]. Sensitive organic membrane layers generally applied in the fabrication of a huge number of chemical sensors have the advantages of high sensitivity, fast response time and being highly selective. The deposition of a sensitive organic membrane layer on the surface of disposable plastic screen-printed microchips is a big challenge and requires sophisticated technological strategies including highly professional servicing. Great attention has been paid and many attempts have been made by scientists to fabricate plastic screen-printed microelectrodes with a sensitive organic membrane layer. Unfortunately, most of these attempts have failed and have not been successful.

It has been noticed over time that the need for the assessment of toxic metals and in particular lead has increased tremendously and has gained significant importance due to the harmful effects of lead on the environment and to human beings. The methods for the determination of lead and other toxic elements, that are in current use that are disclosed in the prior art require sophisticated and expensive machines.

Based on the above-mentioned facts, fabrication, characterization and application of the screen-printed based electrodes to determine lead has become a very interesting challenge for many scientists. Various screen printed modified electrodes have been reported to present promising and cost effective devices for accurate and precise analysis of environmental, biomedical and industrial interest species in different disciplines of samples [12-16].

The present invention discloses a method to fabricate a type of screen-printed microchip based on a nanostructure sensitive organic membrane layer, which is responsive to lead(II). The nano-composite material is embedded in a plasticized PVC membrane and is deposited on the surface of a microchip substrate using a novel, simple, fast and economical approach. The resulting lead(II) screen-printed microchip provides high sensitivity, fast response time, simple fabrication, low cost and automation and integration feasibility. It represents a simple, cheap, miniaturized and mass production tool or device for lead(II) measurements. The micro-fabrication, potentiometric characterization and analytical application of the prepared sensor are demonstrated in this invention.

It would be desirable to provide improved sensor devices. For example, it would be advantageous to improve sensing accuracies, increase production and operation efficiencies, and extend the useful life of the sensor, while minimizing the device size for ease of use and cost of manufacture. The present invention discloses a method and application to achieve the desirable qualities of an electrochemical sensor.

SUMMARY OF THE INVENTION

The present invention discloses a sensor device and a method of preparing thereof, and that the sensor device is used for sensing lead(II) levels. More specifically, the subject matter discloses screen-printed based micro-sensors or microchips where screen printed microchips comprise screen-printed electrodes which are substrates widely used in the fabrication of chemical sensors which are responsive for biological species, drug, toxic elements or heavy metals. These microchip potentiometric sensors work as analytical devices and are especially useful for various medical and environmental measurements carried out at remote sites (infield or in situ determination) as well as in the continuous monitoring of the tested species. The sensor device of the preferred embodiment addresses the problems of determination of lead(II) that causes toxicity to the health and environment. In one embodiment of the present invention a method is disclosed to fabricate a screen-printed microchip, which possesses a nanostructure based organic layer that is sensitive to lead. Heavy metals are generally considered to be of sufficient distribution and abundance as to be in some way environmentally or biologically significant as a toxic substance. Heavy metals may originate from various types of sources such as mining, energy and fuel production, fertilizer and pesticide industry, metallurgy, electroplating and atomic energy installation etc. Heavy metals in industrial and municipal effluents are important sources of water, health and environmental contamination. Lead (Pb) is the one of the most hazardous to human health and environment. The Pb (II) cation also referred to as $Pb^{2+}$ inhibits biosynthesis and affects the kidneys, brain cells and liver membrane permeability, reducing some of their functions. It can be accumulated in the body and can promote disturbances such as nausea, vomiting, diarrhea, coma and death. Lead pollution has influenced the quality of life and may cause serious health problems to both humans and animals. Therefore, it is necessary to develop sensitive methods for determining lead(II) in contaminated samples. Various techniques such as inductively coupled plasma mass spectrometry, luminescence quenching, voltammetry, chemometry, flame atomic absorption spectrometry, and other spectrophotometric methods have been applied for the determination of lead in toxic samples. These methods are expensive and require sophisticated machines, tedious procedures and frequent calibration. Few ion selective electrodes have been reported for determination of lead(II), although such devices offer several advantages such as simple instrumentation, ease of preparation and procedures, reasonable selectivity, relatively fast response, wide dynamic range, and low cost.

On the other hand, micro-sensors originating from chemical sensors have the advantages of reduced size, small sample volume and the integration and automation feasibility. The development of microchip based potentiometric sensors play an important role in toxic metal analysis due to their simplicity, rapidity and accuracy over some other analytical methods. Moreover, micro-sensors generally incorporate some sort of modern technology such as the minimum sample volume and can be used in difficult applications. The advantages brought by these new microchips based sensors are; small and inexpensive; mass-produced, accurate and robust, use of only small amounts of reagents and short response times.

In one embodiment of this invention a method is disclosed for the micro-fabrication of an organic membrane based micro-sensors. In some embodiments of the invention the method disclosed is based on the nebulization of a sensing material, which is a composite nano-particles based organic cocktail coating mixture, on a microchip substrate. This new methodology leads to organic membrane based microchip sensors with excellent life, stability, reproducibility and accuracy. In one embodiment of this invention a method is provided for fabricating a lead(II) micro sensor device which is a microchip comprising the steps of preparing a mixed composition of a sensitive organic membrane material based on a nanocomposite material, nebulizing the organic membrane layer on a microchip substrate and air drying to obtain an even uniform layer of the organic membrane layer which is responsive to lead(II).

In another embodiment of the present invention four microelectrode assemblies or microchips comprising different ratios of the nano-composite sensitive organic membrane materials were made and tested as $Pb^{2+}$ microelectrodes/microchip. In some embodiments of the present invention different compositions of the sensitive organic membrane layer were examined by combining the nanocomposite sensitive material and $TiO_2$ in different ratios in order to select the combination ratio that had the highest Nernstian sensitivity towards $Pb^{2+}$ and showed the most sensitivity to function as micro sensor for $Pb^{2+}$.

In one embodiment of the present invention the ability of the micro sensor devices or microchips to detect the primary $Pb^{2+}$ ion in the presence of other interfering ions which are normally found in toxic waste samples was assessed by measuring the potentiometric selectivity coefficient.

In another embodiment of the invention the reliability and credibility of the fabricated organic membrane based screen-printed $Pb^{2+}$ microelectrode are applied for the analytical potentiometric determination of $Pb^{2+}$ in some aqueous samples.

Finally, the present invention is described further in the detailed description to further illustrate various aspects of the present invention.

BRIEF DESCRIPTION OF THE FIGURES

Example embodiments are illustrated by way of example and not limitation in the figures of the accompanying drawings, in which like references indicate similar elements and in which.

Others features of the present embodiments will be apparent from the accompanying drawings and from the detailed description that follows.

DETAILED DESCRIPTION

The following embodiments are described for illustrative purposes only with reference to the Figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

In order to provide a clear and consistent understanding of the terms used in the present disclosure, a number of definitions are provided below. Moreover, unless defined otherwise, all technical and scientific terms as used herein have the same meaning as commonly understood to one of ordinary skill in the art to which this disclosure pertains. The use of the word "a" or "an" when used in conjunction with the term "comprising" in the claims and/or the description may mean "one", but it is also consistent with the meaning of "one or more", "at least one", and "one or more than one". Similarly, the word "another" may mean at least a second or more. As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unmentioned elements or process steps. As used herein, when referring to numerical values or percentages, the term "about" includes variations due to the methods used to determine the values or percentages, statistical variance and human error. Moreover, each numerical parameter in this application should at least be construed in light of the number of reported significant digits and by applying ordinary rounding techniques. The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Experimental

All the chemicals and reagents used were of analytical reagent grade, unless otherwise stated. Further, double distilled water with Aquatron water distiller (A4000D, Bibby Scientific, UK, 1.0 MΩ cm$^{-1}$) was used in the preparation of the reagents and to rinse the glassware throughout. All reagents used in characterization studies were prepared from analytical reagent grade chemicals in double distilled water. Nitrate or chloride salts of the metal used were purchased from Riedel-de Haën. Plastic screen-printed micro-chips (0.25 mm PET, 3 mm/6 mm in diameter working carbon electrode, SPE modified with graphene) was purchased from Suzhou Delta-biotech (Ltd, China) and used as the substrate microelectrode. Titanium (IV) oxide (TiO$_2$) anatase (99.9%, 32 nm) powder was purchased from Alfa Aesar (GmbH, Germany). Lipophilic additive potassium Tetrakis(4-chlorophenyl) borate and solvent mediator, 2-nitrophenyl octyl ether were purchased from Sigma-Aldrich (CH-9471 Buchs, Switzerland). Purified multiwall carbon nano-tube (CNT) (purity: >95%, id: 5-12 nm, od:30-50 nm, length: 10-20 µm) was purchased from Chengdu Organic Chemicals Company "COCC", China. THF (tetrahydrofurane) and high molecular weight (220,000) poly(vinyl chloride) carboxylated (PVC) were purchased from Riedel-de Haën chemical Company (Germany). All measurements were carried out at room temperature.

Instrumentation and Apparatus

The potentiometric characterization experiments were performed using a Jenway (model 3510) pH/mV meter using a nano-composite based microelectrode as the indicator electrode responsive for lead(II) in conjunction with a Metrohm Ag/AgCl double junction reference electrode. The accuracy assessment study was conducted using a Thermo Scientific (iCAP 7000 series, USA) inductively coupled plasma-atomic emission spectrometer (ICP-AES) instrument supported by Qtera software and connected to a Cetac (ASX-520) auto-sampler. In such studies, a radial mode at 460-379 nm under optimized plasma parameters (RF power: 1150 w, nebulizer gas and auxiliary gas flow: 0.5 L/min) was applied. Further, the surface morphology study of the lead (II) microelectrode was conducted using an analytical scanning electron microscope (JEOL, model JSM-6390 LA). The diameter of the sensitive element nano-particles was studied by a transmutation electron microscope (JEOL model JEM-1011).

Micro Fabrication of Nano-Composite Based Lead(II) Microchip

In one embodiment of this invention the deposition of a sensitive organic membrane layer on a plastic screen-printed microchip, which acts as a substrate was performed, using a simple, fast and cost effective technique. The preparation process of a microchip or microelectrode to create a microchip sensor for a specific purpose is also referred to as a microelectrode assembly.

Figure 1:
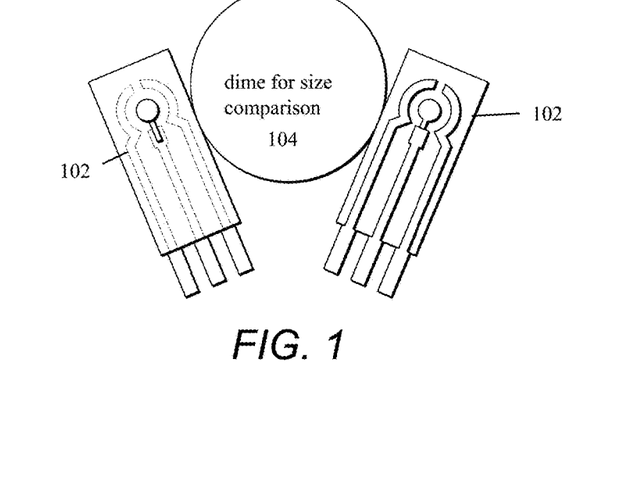
FIG. 1 illustrates a photographic image of a screen-printed microelectrode substrate.
Figure 2:
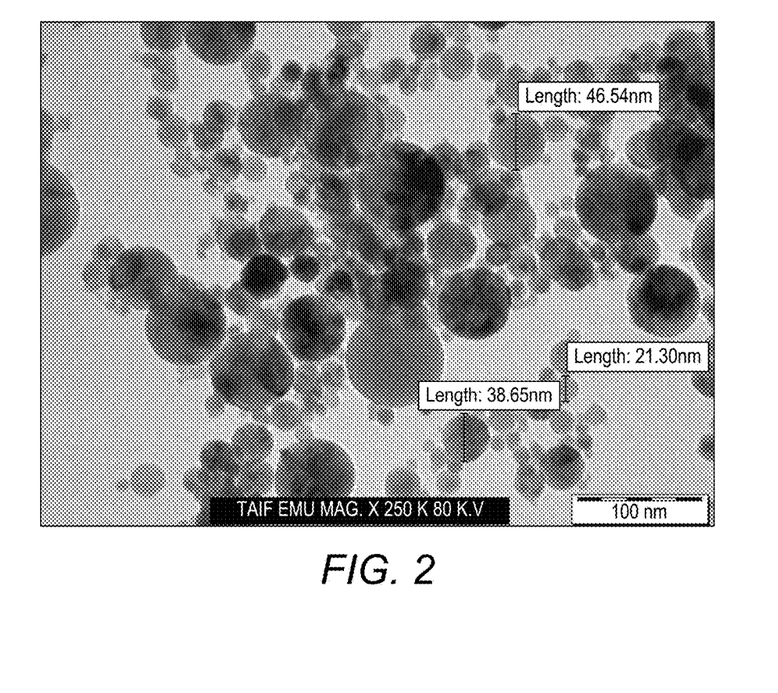
FIG. 2 presents typical TEM of titanium (IV) oxide nano-particles.
Figure 3:
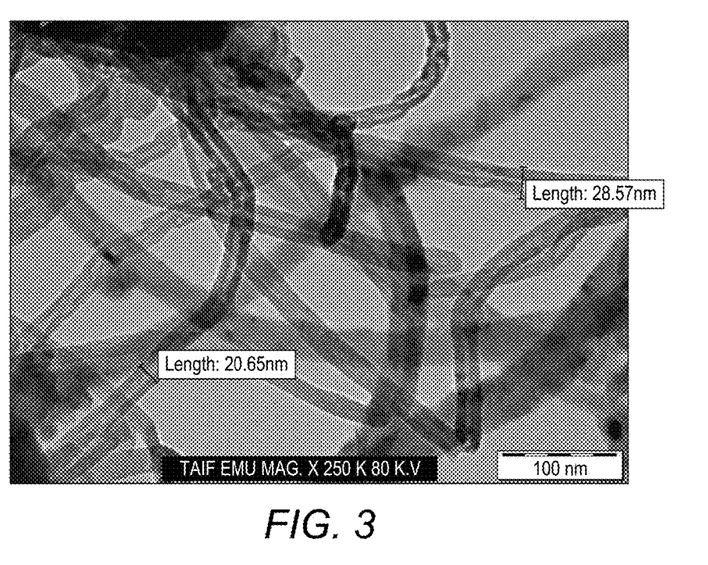
FIG. 3 presents a typical TEM of a carbon nano-tube (CNT).
Figure 4:
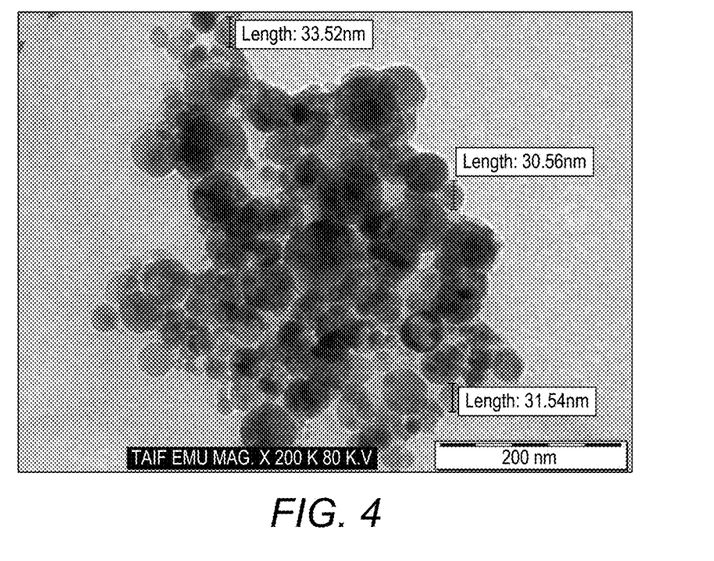
FIG. 4 presents a TEM of titanium (IV) oxide/carbon nano-tube composite in PVC membrane.

In one embodiment, the disposable plastic screen-printed microchip (FIG. 1) was rinsed in double-distilled water and left to air dry before being used as an electrode support or substrate for the microchip. FIG. 1 shows the microchip (102) that was made and shown to compare with a dime coin for size (104).

In another embodiment of this invention an ion pair complex sensitive material or ionophore was prepared by mixing different ratios of the purified multiwall carbon nano-tube (CNT) and Titanium (IV) oxide (TiO$_2$), to obtain the plasticized composite nano-particles ionophore.

In another embodiment of this invention the cocktail coating mixture for each assembly, was prepared by thoroughly mixing 14 mg of the plasticized composite nano-particles ionophore, 6 mg of potassium Tetrakis (4-chlorophenyl) borate, 114 mg of anion excluder and 66 mg of PVC support in 6 mL of THF solvent in a small beaker. This cocktail coating mixture was used as the sensitive organic membrane layer. The cocktail mixture was transferred into a small manual homemade nebulizer and sonicated for 2 hours in order to ensure that the nano-particles were being spread out evenly. This sonication was performed before the cocktail coating mixture was used as the sensitive organic membrane layer.

The microchip in the present invention was prepared by the nebulization of the cocktail coating mixture on the substrate surface of the cleaned microchip. In another embodiment of this invention deposition of the cocktail coating mixture to form the sensitive organic membrane layer was performed in two steps (a) a few micro-liter aliquots of the organic membrane coat was nebulized for a few seconds onto the surface of the screen-printed microchip in the fume hood; (b) in order to achieve volatilization of the solvent the very thin layer of the deposited coating was air-dried for 3 min. The last two steps, (a) and (b) were repeated multiple times until a uniform layer of the sensitive organic membrane layer covered the plastic screen printed microchip substrate surface. In some embodiments of the invention further even spreading of the nano-particle mixture or the sensitive organic material cocktail coating mixture was achieved by sonicating for 3 min between the successive nebulization steps as well. After fabrication, the microchip was then air dried and used as a sensitive microsensor in the potentiometric measurements of lead(II). All potentiometric measurements were performed using the fabricated lead(II) based microchip as the working electrode in conjunction with the commercial Ag/AgCl reference electrode immersed in stirred test solutions. Both the selectivity coefficient K pot (obtained by separate solution A,B method) and response characteristics of the organic membrane layered lead(II) have been measured according to IUPAC recommendations. The fabricated microchips were calibrated by measuring the cell potential values after stabilization to ±0.5 mV in a series of lead(II) solutions. The obtained calibration plot was used for subsequent lead(II) determination. In one embodiment of the present invention the above disclosed method is used to prepare a microchip which functions as a lead(II) micro sensor device composed of a microchip substrate coated with a layer of the sensitive organic membrane material based nanocomposite material, which is responsive to lead(II) ($Pb^{2+}$). The preparation process of a microchip or microelectrode to create a microchip sensor for a specific purpose is also referred to as the microelectrode assembly.

In another embodiment this methodology was used to prepare four microelectrode assemblies, which were prepared and characterized as lead(II) microelectrodes or microchips. The four microelectrode assemblies comprised different ratios of the sensitive nano-composite material, CNT and $TiO_2$ were made and tested as lead(II) microelectrodes/microchips. In one embodiment of this invention several compositions of the ion pair complex or ionophore were prepared by mixing different ratios of the purified multiwall carbon nano-tube (CNT) and Titanium (IV) oxide ($TiO_2$), to obtain the plasticized composite nano-particles ionophore. The composite nano-particles ionophore comprised a mixture composed of at least one material selected from the group consisting of 0-30 w/w % of CNT and 70-100 w/w % of TiO2. In one embodiment of the present invention the first microelectrode assembly resulting in microchip 1 was fabricated wherein the composite nano-particles ionophore comprises a mixture composed of 0 w/w % of CNT and 100 w/w % of TiO2; the second microelectrode assembly resulting in microchip 2 was fabricated wherein the composite nano-particles ionophore comprises a mixture composed of 5 w/w % of CNT and 95 w/w % of TiO2; the third microelectrode assembly resulting in microchip 3 was fabricated wherein the composite nano-particles ionophore comprises a mixture composed of 10 w/w % of CNT and 90 w/w % of TiO2; and the fourth microelectrode assembly resulting in microchip 4 was fabricated wherein the composite nano-particles ionophore comprises a mixture composed of 30 w/w % of CNT and 70 w/w % of TiO2. The compositions of the sensitive organic membrane layers in these microchips are summarized in Table 1. In one embodiment of this invention the prepared microelectrode assemblies were used as lead(II) microchips in characterization and application studies. The microelectrode assemblies or microchips are known as Microchip 1, Microchip 2, Microchip 3 and Microchip 4, depending on their ratio composition, as shown in Table 1.

TABLE 1

Composition of microelectrode lead(II) assemblies.

| Number | Ionophore composite (14 mg) | | AnionExcluder | ONPOE | PVC |
| --- | --- | --- | --- | --- | --- |
| | CNTs % | $TiO_2$ % | mg | mg | mg |
| Microchip 1 | 0 | 100 | 6 | 114 | 66 |
| Microchip 2 | 5 | 95 | 6 | 114 | 66 |
| Microchip 3 | 10 | 90 | 6 | 114 | 66 |
| Microchip 4 | 30 | 70 | 6 | 114 | 66 |

Results and Discussion

The deposition of the sensitive organic membrane layer onto the plastic screen-printed substrate (organic membrane onto organic substrate) was micro-fabricated using a novel and simple technique. The prepared microelectrode was electrochemically characterized according to IUPAC recommendations as a lead(II) potentiometric sensor chip. The advantages provided by the prepared microelectrode results from the combination and interaction of the screen-printed microchip substrate with the sensitive organic membrane layer. Screen-printed microchips have the advantages of small size, mass production, simple construction, versatile applications and being inexpensive. Sensitive organic membrane layers are widely used in many chemical sensors due to their advantages, which include high sensitivity, selectivity and simplicity. In this invention a new generation of screen printed microchips prepared by this methodology is disclosed which has the advantages of both the organic membrane layer and the screen-printed microchip. It is possible for a huge number of organic membrane based microelectrodes to be prepared using the methodology disclosed in this invention. The organic membrane based microelectrodes can be prepared to be responsive for biological species, drugs, toxic elements, heavy metals and pollutants. The device prepared is of a small sized which will improve the automation and integration feasibility and therefore, enhanced the application of such microchips in network sensors. The size and cost advantage will also enable single unit use of the microchip disclosed in this invention.

Characterization of the Sensitive Nano-Composite Material on the Microchip

The organic membrane based thin-film microchip was realized, characterized and examined as a new micro-sensor responsive for $Pb^{2+}$. Prior to the potentiometric characterization of the proposed microchip, the surface morphology studies of the thin-film substrate before treatment, after treatment and after applying the sensitive organic membrane layer were conducted using a transmission electron microscope (TEM) and the scanning electron microscope (SEM). The results obtained are presented in FIGS. 2 to 5. The high resolution of TEM and SEM, which far exceeds that of other optical methods, makes it superior in studying surface morphology.

The particle sizes of $TiO_2$, CNT's and the titanium (IV) oxide/carbon nano-tube composite in PVC membrane was measured using a transmission electron microscope (TEM) to obtain a TEM scan, referred to also as TEM. The results obtained are presented in FIGS. 2, 3 and 4 respectively. As can be seen, the diameters of the particles are relatively uniform and in the nano-scale range with an average size of ~30 nm.

Figure 5:
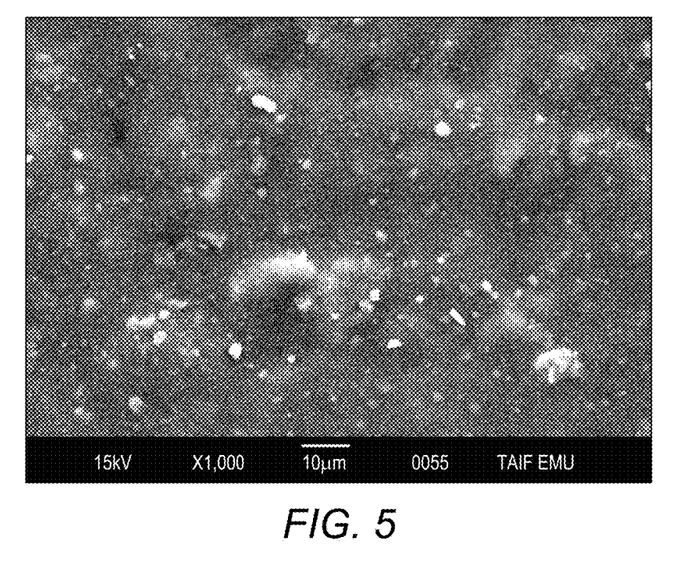
FIG. 5 presents a scanning electron microscope (SEM) image of the sensitive organic membrane layer.

A typical scanning electron microscopy SEM picture of the $TiO_2$ nano-particles/carbon nano-tubes composite after being embedded in the organic membrane and being deposited on the surface of the screen printed substrate is presented in FIG. 5. As clearly seen in FIG. 5, the nano-particles of the composite sensitive material are uniformly distributed on the surface of the screen-printed microchip substrate with some bright aggregations of the polymeric support. The homogenously distributed nano-particles of the sensitive organic membrane layer leads to good sensing properties of the microchip.

Electrochemical Evaluation of the Lead(ii) Microelectrode

Microchips 1 to 4 as described in Table 1 comprise of four different assemblies of the organic membrane based screen printed electrode, having the same content of PVC support, solvent mediator and anion excluder but with different compositions of the sensitive organic membrane layer. The microchips have been fabricated and electrochemically evaluated as lead(II) ($Pb^{2+}$) microelectrode according to IUPAC recommendations. All potentiometric measurements were performed using the fabricated organic membrane based microchip as a working electrode in conjunction with a commercial reference electrode immersed in stirred test solutions. Both the selectivity coefficient K pot (obtained by separate solution A, B method) and response characteristics of the film of the organic membrane have been measured according to IUPAC recommendations. The potentiometric calibration graphs of the four assemblies have been presented in FIGS. 6 to 9.

Figure 6:
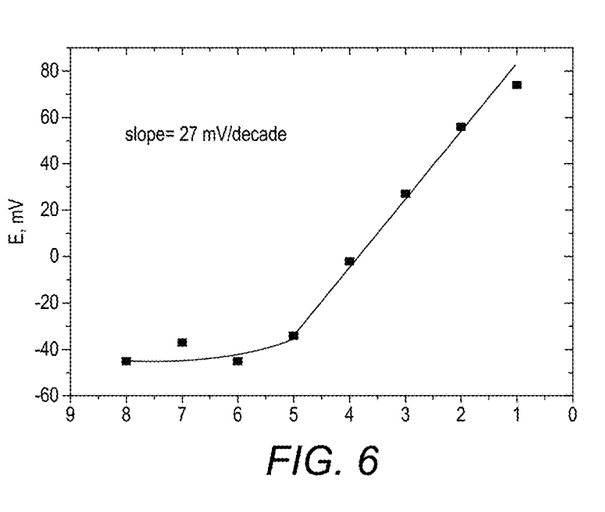
FIG. 6 is a plot of the potentiometric response of the lead(II) microchip known as Microchip 1.
Figure 7:
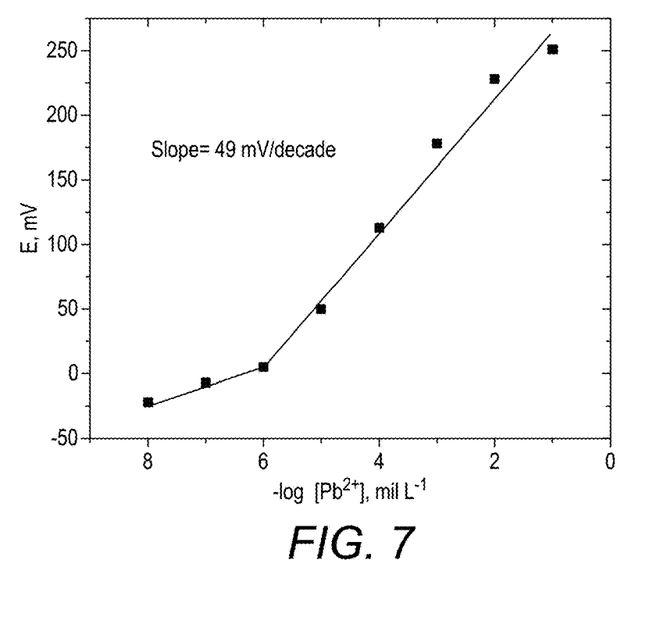
FIG. 7 is a plot of the potentiometric response of the lead(II) microchip known as Microchip 2.

Microchip 1 which is the screen-printed electrode which is based solely on $TiO_2$ without CNTs offers a near Nernstian response for $Pb^{2+}$ ions with a sensitivity of 27 mV/concentration decade as shown in FIG. 6. Addition of CNTs to the sensitive organic membrane layer element (5% CNTs, 95% $TiO_2$) as shown in microchip 2 significantly enhances the sensitivity of the microelectrode increasing it to 49 mV/concentration decade as shown in FIG. 7. It is seen that the microchip 2 provides super Nernstian sensitivity towards $Pb^{2+}$. The increase in the sensitivity of the microchip upon addition of carbon nano-tube is attributed to the interesting and unique properties of the nano-structured materials, which is induced by the high surface to volume ratio. Such materials provide excellent ion-exchange properties and superior electrical conductivity.

Figure 8:
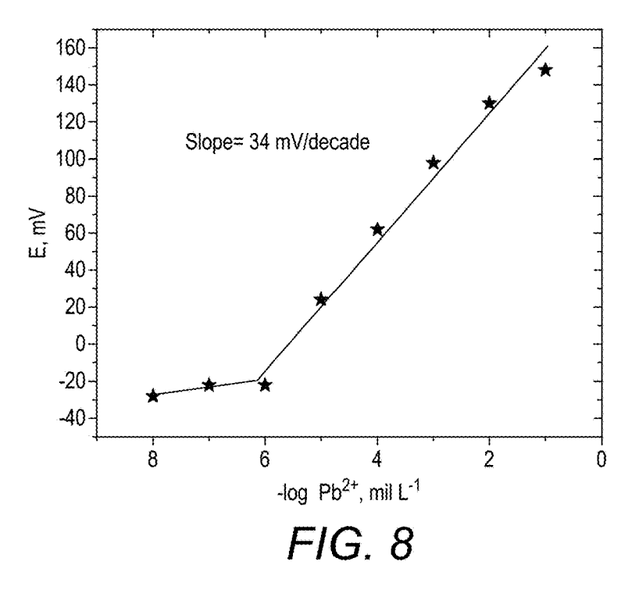
FIG. 8 is a plot of the potentiometric response of the lead(II) microchip known as Microchip 3.
Figure 9:
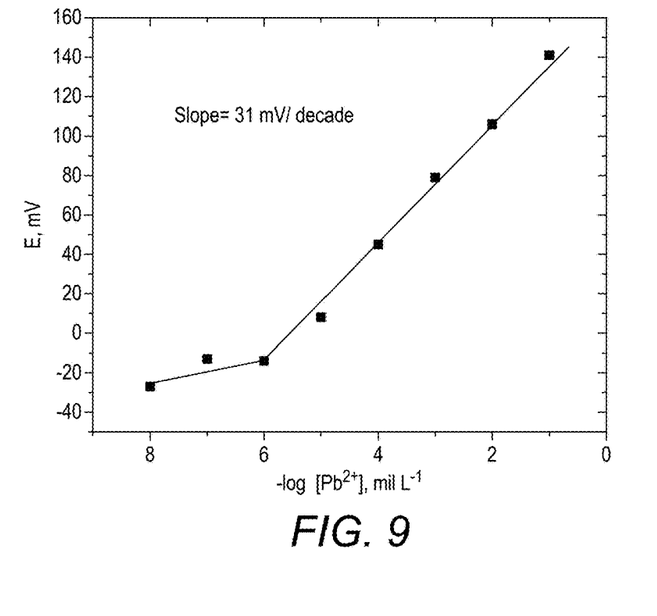
FIG. 9 is a plot of the potentiometric response of the lead(II) microchip known as Microchip 4.
Figure 10:
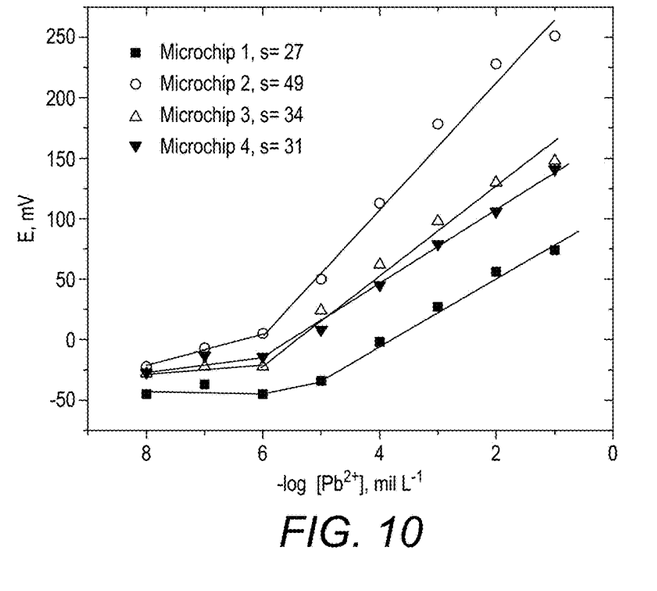
FIG. 10 comprises plots of the potentiometric responses of the lead(II) microchips known as Microchip 1, Microchip 2, Microchip 3 and Microchip 4.

It is seen that in microchips 3 and 4 on increasing the CNTs content in the composite sensitive material there is a gradual decrease in the sensitivity of the microelectrode towards $Pb^{2+}$ ions. This gradual decrease is shown in FIGS. 8 and 9 and is because of the decreasing percentage of the $TiO_2$. Microchips 3 and 4 containing 10% and 30% CNTs respectively, provide a Nernstian response with sensitivities of 31 and 34 mV/concentration decade, respectively as shown in FIGS. 8 and 9. For comparison, the potentiometric calibration graphs of the four microchips were presented in FIG. 10. It is observed that microchip 2 which is the microelectrode that comprises 5% CNTs and 95% $TiO_2$ in its sensitive membrane provides the highest sensitivity with a slope of 49 mV/concentration decade. In one embodiment of this invention this electrode assembly comprising the concentrations of microchip 2 has been proved to be the microchip with optimal performance. Microchip 2 has been selected for the rest of the characterization and application experiments. The potentiometric response characteristics of microchip 2 are summarized in Table 2.

TABLE 2

Response parameters of the $Pb^{2+}$ microelectrode

| Parameter | Response of Microchip 2 |
| --- | --- |
| Slope, mV/decade | 49 ± 1 |
| Linear range, mole $L^{-1}$ | $10^{-6}$-$10^{-1}$ |
| Detection limit, mole $L^{-1}$ | $5 \times 10^{-7}$ |
| Response time, s | 10 |
| Life span, months | >4 |
| pH range | 4-6 |

Based on the mentioned response parameters, the prepared $Pb^{2+}$ microchip 2 offers electrochemical characteristics comparable—and better in some parameter—with those reported for the bulk lead(II) electrodes. Further, the microchip of the disclosed invention has the advantages of reduced size, small sample volume, and integration and automation feasibility.

Figure 11:
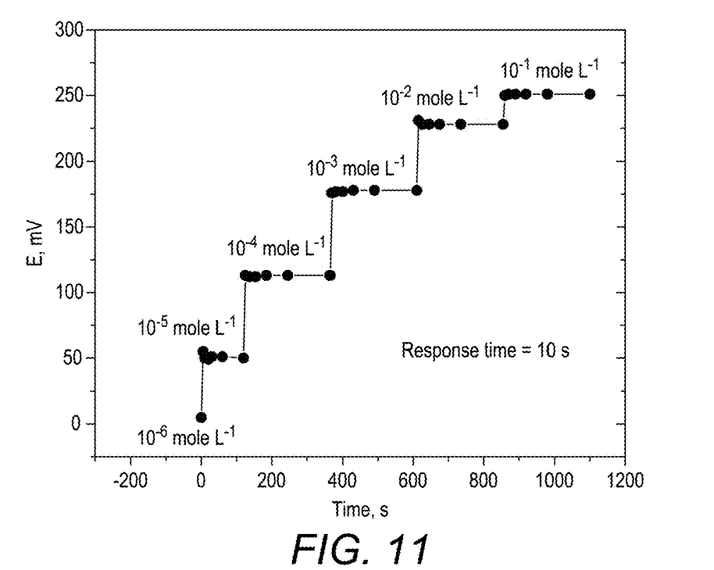
FIG. 11 is a plot of the potentiometric dynamic response of the lead(II) microchip labeled as microchip 2.

The dynamic response time of a micro sensor is defined as the length of time at which the potential reading has reached 95% of the final potential that was investigated. The dynamic response time of microchip 2 was investigated by monitoring the time required to obtain the steady state potential after successively dipping the electrode assembly in a series of $Pb^{2+}$ solutions, each solution having a tenfold increase in concentration from $10^{-6}$ to $10^{-1}$ mole $L^{-1}$. The results obtained are shown in FIG. 11 and it is observed that the nano-composite based microelectrode provides a very fast response time (10 s) in the linear range. Further, the frequent calibration of the microchip reveals that it shows a long life span (>4 months).

Figure 12:
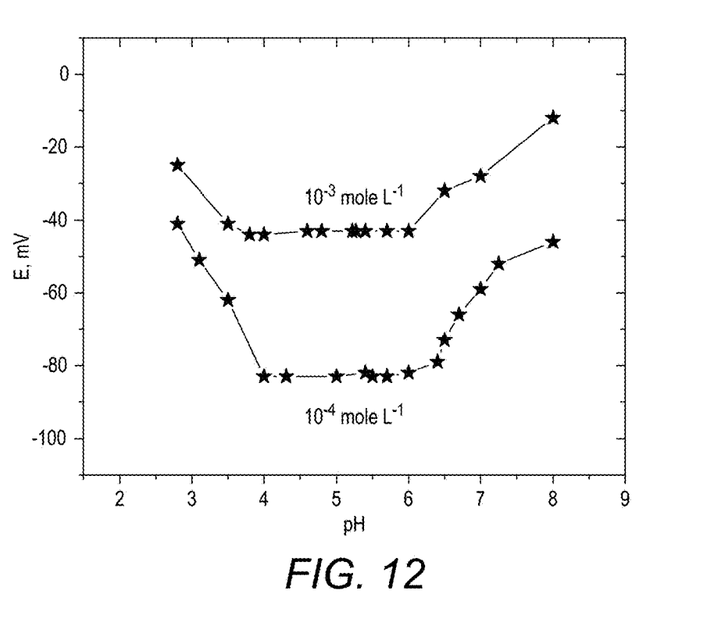
FIG. 12 is a plot of the effect of pH on the potentiometric response of the lead(II) microchips.

The influence of the pH of the test solution on the potentiometric response of the $Pb^{2+}$ microelectrode, which is microchip 2 was investigated for two different concentrations ($10^{-3}$, $10^{-4}$ mole $L^{-1}$). Small aliquots of diluted nitric acid and sodium hydroxide were used to change the pH of the test solutions. The potential change of the microchip (mV) was recorded versus the pH of the test solutions and the data obtained was presented in FIG. 12. The results indicate that, the potential of the microchips is independent of the pH changes in the range from 4 to 6 and consequently this invention discloses the applicability of the microchip 2 to be in this particular pH range. Thus, the characterization and applications studies were conducted in this pH range. The obtained high potential at lower pH values may be attributed to the interference of higher concentration of the hydronium ion, while at higher pHs the high concentration of hydroxyl ion deteriorates the membrane coat.

The ability of microchip 2 to detect the primary ion in the presence of some interfering ions was assessed by measuring the potentiometric selectivity coefficient using a separate solution method (SSM). The results obtained are tabulated in Table 3 and reveal that microchip 2 provides reasonable selectivity towards $Pb^{2+}$ in the presence of the tested monovalent, divalent and trivalent cations.

TABLE 3

Selectivity coefficient of lead(II) screen printed microchip

| Ion | $K_{A,B}^{pot}$ |
| --- | --- |
| $Pb^{2+}$ | 1 |
| $Li^{1+}$ | $1.7 \times 10^{-2}$ |
| $Cr^{3+}$ | $5.2 \times 10^{-7}$ |
| $NH_4^+$ | $1.1 \times 10^{-2}$ |
| $Mg^{2+}$ | $1.6 \times 10^{-5}$ |

TABLE 3-continued

Selectivity coefficient of lead(II) screen printed microchip

| Ion | $K_{A,B}^{pot}$ |
|---|---|
| $Cd^{2+}$ | $1.4 \times 10^{-5}$ |
| $Fe^{3+}$ | $7.9 \times 10^{-6}$ |
| $Ca^{2+}$ | $1.6 \times 10^{-4}$ |
| $Na^+$ | $1.6 \times 10^{-2}$ |

Analytical Application: In order to assess the reliability and credibility of the prepared organic membrane based screen-printed $Pb^{2+}$ microelectrode, the microchip 2 was successfully applied for the determination of $Pb^{2+}$ in some aqueous samples. The $Pb^{2+}$ in these samples was also determined using inductively coupled plasma—atomic emission spectrometry ICP-AES, for comparison. The data obtained is summarized in Table 4. It is observed that the concentration values for $Pb^{2+}$ determined by the micro-fabricated microchip 2, disclosed by this invention are in good agreement with those obtained with the independent ICP-AES method and the average recovery of the study is 101.9%.

TABLE 4

Determination of $Pb^{2+}$ using the four different Microchips

| Number of samples | Microchip 2, ppm | ICP ppm | Recovery % |
|---|---|---|---|
| 1 | 0.21 | 0.21 | 100 |
| 2 | 1.65 | 1.65 | 100 |
| 3 | 20.72 | 19.76 | 104.8 |
| 4 | 103.60 | 100.6 | 102.9 |
| Average recovery | | | 101.9 |

The results are based on three replicate measurements

The micro-fabrication, electrochemical evaluation and analytical application of a novel organic membrane based screen-printed chip responsive for lead(II) has been disclosed in this invention. The disposable microchip has been prepared, using a nebulization methodology that has been developed. The fabricated micro-sensor provides high sensitivity, good selectivity, short response time, a long life span and automation and integration feasibility. Accordingly, the specification and drawings are to be regarded in an illustrative rather than a restrictive sense.

What is claimed is:

1. A method for making a microchip used for a potentiometric determination of lead (II), comprising the steps:
   a. rinsing in double-distilled water a plastic microchip and air drying the plastic microchip to obtain a cleaned plastic microchip;
   b. preparing a composite nano-particles ionophore which made up of a combination of carbon nano-tube (CNT) and Titanium (IV) oxide ($TiO_2$), wherein the composite nano-particles ionophore comprises a mixture composed of 5 of CNT and 95 w/w % of $TiO_2$;
   c. preparing a cocktail coating mixture by adding the composite nano-particles ionophore, potassium Tetrakis (4-chlorophenyl) borate, anion excluder and polyvinyl chloride; and
   d. adding the cocktail coating mixture on to the surface of the cleaned plastic microchip as a substrate by the process of nebulization, to form an evenly layered sensitive organic membrane layer; wherein the evenly layered sensitive organic membrane layer functions as a lead(II) micro sensor device, which is responsive to lead(II) ($Pb^{2+}$).

2. The method as claimed in claim 1, wherein the cleaned plastic microchip is a disposable plastic screen-printed microchip.

3. The method as claimed in claim 1, wherein the cocktail coating mixture is obtained by mixing the composite nano-particles ionophore, potassium Tetrakis (4-chlorophenyl) borate, anion excluder, poly (vinyl chloride) (PVC) support in tetrahydrofurane as a solvent.

4. The method as claimed in claim 3, wherein the process of nebulization for addition of the cocktail coating mixture consisting of the steps:
   a. nebulizing a few micro-liter aliquots of the cocktail coating mixture for a few seconds onto the surface of the cleaned plastic microchip, in a fume hood;
   b. air drying the nebulized cocktail coating mixture for 3 minutes in order to volatilize the solvent so that an even layer of the coating is deposited; and
   c. repeating the above steps (a) and (b) multiple times until a uniform layer of the sensitive organic membrane layer covers the surface of the plastic microchip; wherein deposition of the cocktail coating mixture to form the sensitive organic membrane layer that is responsive to lead(II) occurs allowing the microchip to function as a $Pb^{2+}$ micro sensor device.

* * * * *